United States Patent [19]

Costa

[11] 4,065,552

[45] Dec. 27, 1977

[54] METHOD OF DETECTING MALIGNANT NEOPLASMS

[76] Inventor: Giovanni Giacomo Costa, 100 Riley St., East Aurora, N.Y. 14502

[21] Appl. No.: 574,754

[22] Filed: May 5, 1975

[51] Int. Cl.$^2$ ...................... A61K 29/00; A61K 43/00
[52] U.S. Cl. ............................................ 424/1; 424/9
[58] Field of Search ................. 424/1, 9, 1.5; 250/303

[56] References Cited

U.S. PATENT DOCUMENTS

| 3,061,510 | 10/1962 | Numerof et al. | 424/1 |
|---|---|---|---|
| 3,716,631 | 2/1973 | Steggerda et al. | 424/1 |
| 3,717,704 | 2/1973 | Turner et al. | 424/1 |
| 3,818,089 | 6/1974 | Bagley et al. | 424/9 |

FOREIGN PATENT DOCUMENTS

| 701,423 | 1/1965 | Canada | 424/1 |

OTHER PUBLICATIONS

Andrews et al., ed., Radioactive Pharmaceuticals, USAEC Technical Information Center, Oak Ridge, 1966, pp. 553–565.

*Primary Examiner*—Benjamin R. Padgett
*Assistant Examiner*—Christine M. Nucker
*Attorney, Agent, or Firm*—Fidelman, Wolffe & Waldron

[57] ABSTRACT

A diagnostic test method of detecting malignant neoplasms is provided involving administering, to a subject under investigation, a labelled tracer compound capable of being metabolized by the subject. A sufficient period of time is allowed to elapse to permit the subject to metabolize the labelled tracer compound after which time the excretion products of the subject are analyzed for labelled products.

18 Claims, 2 Drawing Figures

CO2 TEST IN VARIOUS DISEASES

14CO2 PRODUCTION IN MICE

METHOD OF DETECTING MALIGNANT NEOPLASMS

BACKGROUND OF THE INVENTION

The present invention relates to a diagnostic test method for detecting malignant neoplasms.

The neoplastic process in human beings has been, and still is, the subject of intensive study. In order to obtain a better understanding of the disease, human cancer tissue has been studied in an effort to discover the cause, treatment, prevention and diagnosis of cancer. Early diagnosis of cancer is very important since it increases chances of effecting a complete remission of the disease.

In an effort to utilize known diagnostic tools to detect the presence of malignant tumors, attempts have been made to demonstrate tumor specific components, such as hormones or antigens. These attempts have been unsuccessful with many types of malignant tumors, since it has not been possible to segregate normal tissue antigens from abnormal cancer antigens and demonstrate the specificity of the cancer antigens or it has not been possible to demonstrate tumor specific components.

In the efforts to isolate abnormal cancer antigens and demonstrate their specificity, attempts have been made to cause the formation of tumor-specific antibodies and demonstrate their presence in sera obtained from animals immunized with preparations of human cancer. If consistently reproducible, the demonstration of the presence of tumor-specific antibodies in animal antisera would lead to the use of a valuable diagnostic tool.

In order to fully utilize the existence of tumor-specific antibodies in animal fluids, a diagnostic test must be developed which will demonstrate the presence of the tumor antigens in the blood of the patient. Procedures which have been devised have not proven efficient or sensitive in the detection of and differentiation between carcinomas originating at different locations in the body, either primary or as a result of metastasis.

Efforts to abstract relatively pure antigens associated with carcinomas have met with either no success or are impractical from a commercial point of view, since a process has not been found to make it possible to completely segregate such as antigen from normal tissue antigens and non-antigenic materials.

Various examples exist in the prior art which are directed to a method of detecting abnormal tissues through the use of radioactively tagged compounds. In a specific example wherein a radioactively labelled compound is used to determine disease tissue, the sample of cells from a body under investigation is treated with a radioactively tagged substance which is determined to be selectively absorbed by one or more predetermined cell types sought to be identified either as disease-producing cells or abnormal cells of the body and distinguished from other cell types. The radioactively tagged substance is absorbed in different amounts by some cells and rejected by other cells. After treatment and washing, the level of radioactivity of the cell sample is sensed in order to determine, from the degree of absorption of the radioactively tagged substance, information about the presence or absence of disease. The technique may be applied to mass screening for disease of a particular type, or types, by collecting and identifying similar samples from many subjects and using a predetermined common standard of radiation level to eliminate those samples which are clearly free from disease. A major disadvantage of the foregoing process is that the procedure involves fixed sample, that is, samples of dead tissue cells or microorganisms, and is best employed where hundreds of samples of the same kind are to be considered. The instant invention is effected through the utilization of living subjects and indicates a relatively high rate of accuracy in identifying malignant neoplasms, which may occur in any part of the subject under investigation.

Other areas of the art relate to methods of isolating and characterizing the antigen components referred to as carcinoembryonic antigens which are associated with various carcinomas to establish diagnostic test procedures. These methods require extensive procedures to enable the components of the carcinoembryonic antigens to be separated and additional processes must be directed to the structural characterization of the carcinoembryonic antigens isolated in addition to a process for the radioactive tagging of the specific antigens of interest. The specificity of this method is very low and detection in the early stages very difficulty since the antigen concentration only increases as the tumor progresses.

OBJECTS OF THE INVENTION

The principal object of the instant invention is to provide a diagnostic test method of detecting malignant neoplasms.

A further object is to provide a diagnostic test method for detecting malignant neoplasms in living subjects without the removal of affected tissue.

Another object of the instant invention is to provide a test method for indicating the early existence of various malignant neoplasms including adenocarcinoma of the colon and digestive tract, carcinoma of the liver, and carcinoma of the breast, cervix, lung, prostrate, esophagus, endometrium, Hodgkins Disease and hypernephroma, to name only a few.

A still further object is to provide a test method for the determination of the presence of malignant neoplasms which provides a positive identification at very early stages to enable appropriate treatment to effect a complete remission of the disease where possible.

A still further object of the invention is to provide a diagnostic test method for detecting malignant neoplasms which involves the use of labelled lipid tracers wherein the excretion products of the subjects under test are analyzed for the presence and concentration of labelled products.

Additionally, it is the object of the instant invention to provide a quick, easily effected, method for determining the existence of malignant neoplasms in any part of the subject.

DETAILED DESCRIPTION OF THE INVENTION

Broadly, the invention relates to a diagnostic test method for detecting malignant neoplasms which involves the administration to the subject, under controlled conditions, of a labelled lipid tracer which is capable of being metabolized by the subject. After administration of the labelled lipid tracer to the subject, an amount of time is allowed to lapse to allow for the metabolism of the lipid tracer. At the end of the lapsed time period, the urinary or respiratory excretion products of the subject are analyzed for labelled products.

Generally, the subject has administered to him, under controlled conditions, an analytically significant amount of a labelled lipid tracer wherein the lipid tracer is generally selected from the group consisting of simple fats, fatty acids, fat precursors, phospholipids, steroids and sterols wherein the labelled tracer atom is generally selected from the group consisting of carbon-14, oxygen-18, deuterium, tritium, phosphorous-32 and carbon-13.

Generally, the time required for the metabolism of the ingested labelled tracer will be from less than one hour to about 30 hours. A fixed time is generally selected for analysis wherein the amount of labelled material to be found in the excretory products is at an optimum.

The analyses of the excretion products can be conducted using any suitable radiochemical method such as photographic emulsion, ionization chambers, geiger counters, proportional counters and scintillation counters.

In the preferred embodiment of the instant invention, the diagnostic test method for detecting malignant neoplasms involves orally administering to a fasting subject, under controlled conditions, from about 3 to 80 microcuries per subject of a carbon-14 labelled simple fat, such as olein, palmitin, (tripalmitin) or stearin. The fasting is continued for a short time and the total waiting period of approximately 14–18 hours is allowed to lapse to allow for the metabolism of the labelled tracer. The respiratory excretion products of the subject of interest are analyzed by slowly bubbling a quantitative amount of the exhaled breath through an ethanolamine/methylcellosolve solution until it is fully saturated with carbon dioxide, adding a scintillation solution, and recording the amount of carbon-14 in a liquid scintillation counter.

The administration of the labelled tracer to the subject can be by any suitable means including oral ingestion, and intravenous or intramuscular injection. The conditions under which the labelled tracer is administered are generally controlled as to the diet and caloric expenditure of the subject under investigation, to prevent any significant changes in the metabolism of any of the subjects investigated. Specific requirements of the individual include fasting to control the relative nutritive intake of each of the subjects and prevention of any unusual and significant amounts of exertion.

The labelled lipid tracers are selected from the group consisting of fat precursors, fatty acids, simple fats, phospholipids, steroids and sterols. The simple fats are mono-, di- and triglycerides of fatty acids wherein the fatty acids have a carbon chain length of from 2 to about 22 carbon atoms and are saturated or unsaturated. The most common fatty acids which unite chemically with glycerol to form a simple fat include, but are not limited to, oleic, palmitic, and stearic acids. The fats formed from the foregoing acids forming the glyceryl ester are called, respectively, triolein, tripalmitin and tristearin. Oleic acid is an 18 carbon fatty acid having a single unsaturation. Palmitic acid is a 16 carbon fatty acid and stearic acid is an 18 carbon fatty acid, both of which are saturated. Various other acids which may be used to form glycerol ester include linoleic, linolenic and arachidonic.

Fatty acids having a carbon chain length of from about 2 to about 22, saturated or unsaturated, may also be used alone, when appropriately labelled, as a tracer. These include, but are not limited to, palmitic, stearic, oleic, linoleic, linolenic and arachidonic. The most common fatty acids are those having an even number of carbon atoms, usually from about 8 to about 22, in a straight chain wherein the chain is saturated or unsaturated.

The most common fat precursor which may be used in the instant invention is the labelled acetate.

Various phospholipids utilizable herein include lecithins, cephalins and sphingomyelins.

Steroids and sterols comprise a large group of compounds having in common a structure based on cyclopentanophenanthrene nucleus. They have greatly diversified physiological properties and include, but are not limited to, such substances as cholesterol, bile acids and hormones.

Carbon-13, carbon-14 and oxygen-18 can be used to label the fat precursors, fatty acids and simple fats. The labelled catabolic products are detected by appropriate analysis of respiratory products, i.e. labelled carbon dioxide or labelled water. It is preferred in the instant invention to label the fat precursors, the fatty acids or the simple fats with carbon-14 at the carboxyl carbon; such compounds are commercially available and analyze the respiratory products for the occurrence and concentration of carbon-14 dioxide.

The phospholipids can be labelled with phosphorous-32 and the labelled catabolic products detected in the urine by suitable analytical procedures sensitive to phosphorous-32. The steroids and sterols can be labelled with carbon-13 or carbon-14, and the catabolic products detected in the urine. Deuterium or tritium may also be used to label any of the foregoing compounds. Their existence in the excretion products would, of course, be in the water, either in the urinary products or in the respiratory products, depending on the compound in which they were initially placed and its metabolic route.

Generally, a waiting period is required after initial administration of the labelled tracer material to allow time for the material to be catabolized and show up in the catabolic by-products to be analyzed. The time generally is a minimum of less than one hour and extends generally to approximately 30 hours. However, it has been found that an optimum time of from about 14 to about 18 hours is sufficient to allow an optimum concentration of the labelled products to appear in the excreta.

The preferred method of detecting the labelled catabolic by-products is through the use of a scintillation counter or by scintillation analysis.

DISCUSSION

The lipids include the following classes of substances of great importance to the human body: simple fats, phospholipids, steroids and sterols.

The simple fats are esters of fatty acids and glycerol. Because of the composition of simple fats, they are valuable purveyors of energy and can be stored in the body as adipose tissue. The fats and fat-like compounds are also useful as solvents for fat soluble vitamins such as vitamins A, D, E and K.

Phospholipids, such as lecithin (phosphotidylcholine), which is the most important phospholipid in the body, is formed when one molecule of a fatty acid in a triglyceride (e.g. in tripalmitin, one of the three fatty acid molecules) is replaced by a complex nitrogenous substance, choline and phosphoric acid. This compound is found in all living cells and seems to be essential for life. The most important members of the phospholipid group are lecithins, cephalins and sphingomyelins.

The term "steroids" refers to a large group of compounds having in common a structure based on the cyclopentanophenanthrene nucleus. They have greatly diversified physiological properties and include such substance as cholesterol, bile acids, important hormones and certain carcinogens.

The first step in the catabolism of simple fat involves its hydrolysis into two main components, namely glycerol and fatty acids. The glycerol portion of the lipids is converted into glyceraldehyde. It enters the chain of reactions and is completely oxidized in the citric acid cycle.

The oxidation of fatty acids involves five essential steps. The principal step is the formation of the active fatty acid by combination with coenzyme-A. This is followed successively by dehydrogenation, hydration, dehydrogenation, and a cleavage reaction. The original carbon chain is reduced by two carbon atoms and the remainder can be recycled, starting at the second step until the entire fatty acid has been converted into acetyl-CoA. Subsequently, the molecules of acetyl-CoA enter the citric acid cycle and are oxidized to carbon dioxide and water with the production of energy.

If the carboxy carbon of palmitic acid is replaced with a labelled atom (e.g., namely carbon-14), followed by formation of the glyceryl triester, catabolism of the tripalmitin (the fat formed by the esterification of glycerol and three molecules of palmitic acid) will result in the formation of a labelled carbon dioxide which can be detected by suitable radiochemical methods. In the preferred embodiment, the radiochemical method used is scintillation detection. The foregoing also applies to the catabolism of fat precursors and fatty acids. The catabolism of phospholipids and steroids follows a more complex path resulting in labelled products which can be detected in the urine alone or in the urine and the respiratory products.

EXPERIMENTAL

Figure 2:
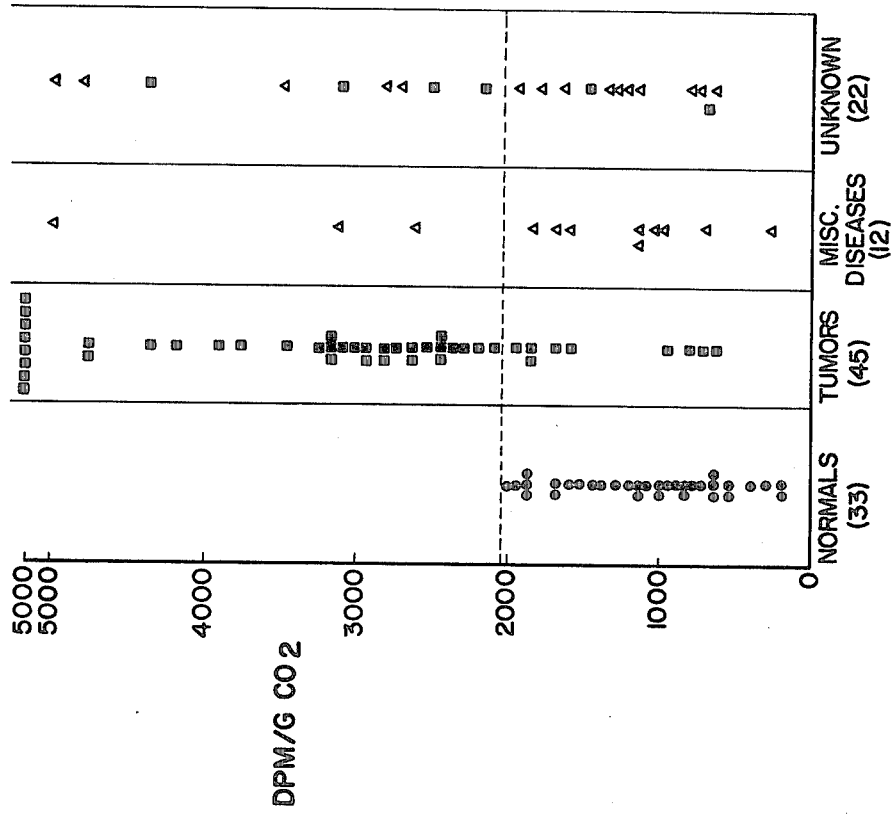
FIG. 2 shows the excretion of carbon-14 dioxide by human subjects.

The invention is to be illustrated by the following examples in which parts and percentages are by weight unles otherwise indicated. These nonlimiting examples are illustrative of certain embodiments designed to teach those skilled in the art how to practice the invention to represent the best mode contemplated to carry out the invention.

INTRODUCTION

Labelled carbon-14 tripalmitin was administered intraperitoneally to mice which had been injected with a Krebs-2 carcinoma, and the rate of excretion of carbon-14 dioxide was studied. The presence of a tumor induced a very significant suppression, by about 80% of formation of the carbon-14 labelled carbon dioxide within 24 hours from the time of the implantation of the tumor in all the animals tested, thus allowing unambiguous identification of the tumor-bearing mice. When human cancer patients were studied along with normal human volunteers and human patients with non-neoplastic diseaases, the labelled carbon dioxide excretion data could be used to identify the cancer patients with an overall accuracy of 84%.

EXPERIMENTAL PROCEDURE

In the following experiments which were conducted utilizing male Swiss mice, the mice ranged by body weight between 25 and 35 grams and were obtained commercially.

The carboxy labelled carbon-14 tripalmitin was obtained from the New England Nuclear Co. of Boston, Mass. and was administered in two forms. For the experiments with mice, the labelled material was dissolved in peanut oil. For the experimental human studies, 50 microcurie aliquots of the tracer, carefully measured, were prepared in capsules suitable for oral administration.

The Krebs-2 carcinoma, a transplantable mouse tumor used in experiments with mice, was obtained originally from the Roswell Park Memorial Institute in Buffalo, N.Y. and carried in its ascitic form in Swiss mice.

To study oxygen consumption and production of total carbon dioxide, i.e. non-labelled and labelled, in mice, a metabolic chamber was used as disclosed by G. Costa, L. Ullrich, F, Kantor and J. F. Holland and entitled "Production of Elemental Nitrogen by Certain Mammals Including Man," Nature 218; 546 (1968) incorporated herein by reference.

Oxygen consumption is calculated from the consumption of electrical current by the electrolytic cell described in the above noted paper by G. Costa, et al. All of the carbon dioxide produced was trapped, in 2 hour aliquots, in a 20% potassium hydroxide solution contained in the wash bottles of the depuration loop which is also described in the paper noted above by G. Costa et al. The volume of each potassium hydroxide solution was then brought to 1 liter with water using volumetric flasks. Duplicate aliquots of these solutions were then used for the determination of the total carbon dioxide and carbon-14 dioxide as follows:

Carbon-14 Dioxide 25 ml aliquots of the potassium hydroxide solution were mixed with 25 mls of 6.0 normal hydrochloric acid solution. The evolved carbon dioxide was trapped in a 5 ml mixture of ethanolamine and methylcellosolve in a ratio of 1:2 by volume using a stream of nitrogen. A 3ml aliquot of the ethanolamine-methyl-cellosolve solution was added to 15ml of scintillation solution, i.e. toluene/-methylcellosolve/PPO(2,5-diphenyloxazole) and counted in a Nuclear Chicago Mark II liquid scintillation counter having an efficiency of approximately 80%.

Total Carbon Dioxide

To determine the total carbon dioxide, the potassium carbonate contained in a 25ml aliquot of potassium hydroxide solution was precipitated as barium carbonate with a 3% solution of barium hydroxide. The precipitated barium carbonate was filtered out using a glass filter crucible, washed with water, dried to a constant weight at 120° C. and measured gravimetrically.

EXPERIMENTS CONDUCTED USING MALE SWISS MICE:

Eight groups of 5 mice injected subcutaneously (on their backs) with either Krebs-2 cells as described above or with an equal volume of saline solution, received intraperitoneally, at appropriate times after the implantation of the tumors, 2 microcuries per mouse of carbon- 14 labelled tripalmitin solution (i.e. 0.2ml per mouse). The injection site was wiped clean and the animals locked in the metabolic chamber, as described in Nature, 218; 546 (1968) referred to above, where they were studied for 24 hours at 28 degrees C. in an air atmosphere with food and water ad libitum. After the completion of the experiments, all tumor-bearing mice were observed until their death to demonstrate that the implanted cancer was indeed growing.

EXPERIMENTS CONDUCTED USING HUMAN SUBJECTS

In the human experiments, the subjects to be studied swallowed, at 8:00 AM precisely, after an overnight fast, a capsule containing 50 microcuries of labelled tripalmitin. Fasting was then continued until noon, after which the subjects were free to eat ad libitum. Samples of expired air were analyzed every 2 hours for 20 to 30 hours as needed.

Normal volunteers were selected among medical school personnel. Their lack of significant disease was supported by history, complete physical examination, routine hematological and chemical determinations, urinalysis, a chest roentgenogram and an electrocardiogram, all of which were obtained in our clinical research center.

To determine carbon-14 dioxide in the human experiments, about 10 liters of expired air was collected in anesthesia bags using a mouthpiece, a one-way valve and a length of standard respirator hose. The carbon dioxide was then trapped in four milliliters of ethanolamine/methylcellosolve (1:3 volume per volume), by bubbling the expired air through the absorption mixture using a Travenol hemodialysis pump which can be obtained from Travenol Laboratories, a division of Baxter Laboratories, located in Chicago, Illinois.

Bubbling of expired air continued until the trapping power of the ethanolamine was saturated, as determined by barium carbonate precipitation in barium hydroxide bottle receiving the overflow gas. A 3ml aliquot of the ethanolamine/methylcellosolve was then counted as described above to determine the carbon-14 dioxide content.

RESULTS OF THE EXPERIMENTS UTILIZING MICE

These eight experiments were conducted with the protocol described above. Of these, three were control experiments, three were conducted with animals bearing 5-day old tumors (i.e. injected with a suspension of tumor cells 5 days previously), one with animals bearing 24-hour old tumors and one with 12-hour old tumors.

Table 1 shows the weights of the mice used in these experiments, total oxygen consumption and total carbon dioxide production.

Hourly oxygen consumption and 2-hourly carbon dioxide production remained reasonably constant for each experiment, throughout the period studied. Small but statistically significant increases of both oxygen consumption and total carbon dioxide production were induced by the tumor. The respiratory quotient (which is the carbon dioxide produced divided by the oxygen utilized and varies in accordance with the fuel utilized) remained unchanged. Thus, a hypermetabolic state was induced by the tumor.

Figure 1:
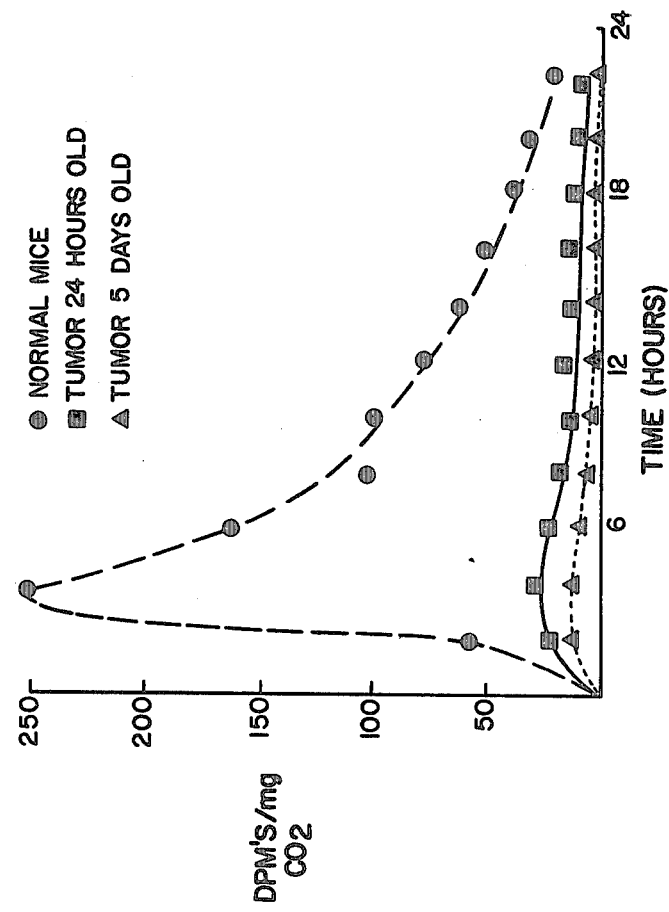
FIG. 1 is a 2-hourly data presentation of carbon-14 dioxide excretion.

FIG. 1 and Table 2 shows the excretion of carbon-14 dioxide (as compared to total carbon dioxide). FIG. 1 presents the 2-hourly data expressed as DPM/mg (disintegrations per minute per milligram) of carbon dioxide. The three representative experiments were conducted with normal mice, mice bearing 5-day old tumors and in mice bearing 24-hour old tumors. Production of carbon-14 dioxide was considerably suppressed in the presence of the tumor. Complete separation of the curves relative to tumor-bearing mice from the controlled curve occurred at all times.

TABLE 1

| | | | $O_2$ CONSUMPTION AND $CO_2$ EXCRETION BY NORMAL AND KREBS-2 BEARING MICE | | |
|---|---|---|---|---|---|
| EXP # | TYPE | WT. OF 5 MICE | $O_2$ CONSUMPTION 1/24h/5 mice | $CO_2$ EXCRETION 1/24h/5 mice | R*** |
| I | CONTROL | 125.6 | 9.32 | 8.39 | 0.90 |
| IV | CONTROL | 152.5 | 9.18 | 8.27 | 0.91 |
| V | CONTROL | 145.0 | 9.20 | 7.90 | 0.85 |
| AVE** | CONTROL | 141.0 ± 13* | 9.23 ± 0.75* | 8.18 ± 0.25* | 0.88 |
| II | Krebs-2 × 5day | 142.6 | 10.00 | 8.83 | 0.88 |
| III | Krebs-2 × 5day | 159.3 | 12.51 | 11.53 | 0.92 |
| VI | Krebs-2 × 5day | 172.3 | 10.56 | 9.45 | 0.90 |
| AVE** | Krebs-2 × 5day | 158.0 ± 15* | 11.02 ± 1.3* | 9.93 ± 1.4* | 0.90 |
| VII | Krebs-2 × 24hr | 186.0 | 10.61 | 8.70 | 0.82 |
| VIII | Krebs-2 − 12hr | 184.0 | 10.18 | 9.38 | 0.92 |
| AVE** | (ALL TUMOR BEARING) | 169.0 ± 18* | 10.77 + 1.0* | 9.57 ± 1.13* | 0.88 |

(probability)
"p" < 0.05 when $O_2$ consumption or $CO_2$ production of control mice is compared to Krebs-2 bearing mice
*Standard Deviation
**AVERAGE
***R = RESPIRATORY QUOTIENT Table 2 presents peak values (expressed in DPM) and cumulative excretion of carbon-14 dioxide (expressed as percentages of the injected dose) for each of the eight experiments. Clear and statistically significant differences were observed between the normal animals and the animals bearing tumors for at least 24-hours. Such changes had not yet developed in animals bearing 12-hour tumors.

The data from Tables 1 and 2 and FIG. 1 indicate that, while the excretion of total carbon dioxide (which was derived at least in part from the animal's own fat) was increased by the presence of the tumor, conversion of the carbon-14 labelled tripalmitin into carbon-14 dioxide was markedly suppressed. No overlap of the carbon-14 dioxide values occurred as early as 24 hours after the implantation of the tumor. The data relative to 12-hour old tumors were not different from the controls.

RESULTS IN EXPERIMENTS UTILIZING HUMANS

The following four groups of human subjects were studied according to the protocol outlines described above:

Group I: 33 normal volunteers;
Group II: 35 patients with a variety of known cancers;
Group III: 12 patients with diseases other than cancer;
Group IV: 22 patients whose diagnosis was undetermined at the time of the study, and in whom cancer was part of the differential diagnosis.

Definitive diagnosis was established in all of the members of Group IV before their discharge from the hospital.

Table 3 shows the types of tumors for the patients of Group 2 and the final diagnosis for the patients of Group 3 and Group 4.

In studying the carbon-14 dioxide excretion curves plotted for 24 hours (not shown), a significant overlap was found in the early hours between the subjects of Group 1 and the subjects of Group 2. It was apparent nonetheless that, although peak values were overlapping, cancer patients continued to excrete carbon-14 dioxide longer. Maximum separation of the curves occurred at 16 hours after administration of the label. Because, at this point, we were focusing primarily on a reproducible difference between cancer patients and all others, a number of patients in Groups 1 and 2, and all of the patients in Groups 3 and 4, were studied with duplicated samples obtained only at the 16th hour.

FIG. 2 shows the excretion of carbon-14 dioxide by human subjects expressed as DPM (disintegrations per minute) per gram of carbon dioxide, 16 hours after the administration of the label.

FIG. 2 shows that the values of the normal subjects averaged $1,114 \pm 520$ DPMs. Thus, the 95% confidence limit of the normal population extends to 2,154 DPM's.

TABLE 3

| HUMAN SUBJECTS STUDIED | | | |
|---|---|---|---|
| GROUP I: | 33 NORMAL VOLUNTEERS | | |
| GROUP II: | PATIENTS WITH KNOWN CANCER | | |
| Tumor Types | | | |
| Carcinoma of Cervix | 11 | Carcinoma of Endometrium | 3 |
| Carcinoma of Lung | 5 | Hodgkins Disease | 2 |
| Carcinoma of Breast | 4 | Hypernephroma | 2 |
| Carcinoma of Prostate | 3 | Other | 12 |
| Carcinoma of Esophagus | 3 | Total | 45 |
| GROUP III: | PATIENTS WITH NON-NEOPLASTIC DISEASES | | |
| Obesity | 5 | Thyrotoxicosis | 1 |
| Cirrhosis | 2 | Pneumonia with Abscess | 1 |
| Systemic Lupus Erythematosus | 1 | Sarcoidosis | 1 |
| Leukocytoclastic Angitis | 1 | Total | 12 |
| GROUP IV: | PATIENTS WITH INITIALLY UNKNOWN DIAGNOSIS | | |
| Neoplastic Diseases | | Non-Neoplastic Diseases | |
| Carcinoma of Lung | 4 | Status Post "various" Carcinomas (No Evidence of Recurrence) | 4 |
| Carcinoma of Prostate | 2 | | |
| Carcinoma of Endometrium | 1 | Cirrhosis | 2 |
| Embryonal Cell Carcinoma | 1 | Other | 8 |
| Total | 8 | Total | 14 |
| | | Combined 22 | |

Thirty-six out of 45 tumor patients in Group II had specific activity falling above the 95% limits of the normal population. The specific activity is defined as

TABLE 2

| CARBON-14 DIOXIDE EXCRETION BY NORMAL KREBS-2 BEARING MICE | | | | |
|---|---|---|---|---|
| | | PEAK VALUE (DPM) | | TOTAL RECOVERY (% OF INJ. |
| EXP | TYPE | ABSOLUTE | DPM/MG $CO_2$ | DOSE/24 HR.) |
| I | CONTROL | 2260 | 109 | 3.44 |
| IV | CONTROL | 5891 | 252 | 5.32 |
| V | CONTROL | 3229 | 127 | 4.92 |
| AVE** | | $3793 \pm 1880$* | $162 \pm 77$* | $4.56 \pm 0.99$* |
| II | Krebs-2 × 5day | 1256 | 36 | 1.88 |
| III | Krebs-2 × 5day | 419 | 18 | 0.60 |
| VI | Krebs-2 × 5day | 491 | 15 | 0.61 |
| AVE** | | $722 \pm 463$* | $23 \pm 11$* | $1.03 \pm 0.73$* |
| VII | Krebs-2 × 24hr | 616 | 21 | 1.16 |
| VIII | Krebs-2 × 12hr | 3480 | 135 | 6.74 |

"p" < 0.05 when either peak values or total recovery from mice bearing 5d Krebs-2 is compared with normal mice.
*Standard Deviation
**AVERAGE DPM's/mg $CO_2$, i.e. carbon-14 dioxide/total carbon dioxide. Nine out of 12 patients with non-neoplastic diseases fell within the normal range.

Of the 22 patients of Group IV (that is, patients with initially unknown diagnoses), seven were finally diagnosed as having a malignant neoplasm. Of these, five out of seven fell above the normal range. Overall, 111 patients and normal subjects were studied. Of these, using the 95% confidence limits of the normal observation, 18 were classified erroneously in terms of presence or absence of cancer. Ninety-two out of 111 were classified correctly with an overall accuracy of 83%. Of the patients studied, forty-nine had specific activities falling above the normal range. Of these, forty-one had a malignant neoplasm (84%).

The results indicate in mice that the presence of the tumor markedly suppresses the conversion of the exogenous carbon-14 tripalmitin into carbon-14 dioxide. The mechanism for this effect is currently not understood and the applicant does not wish to limit himself in accordance with any proposed theory. At the present time, and until such time as new enlightening experimental data are provided, it is the applicant's desire to avoid speculation regarding the theory which causes the phenomenon which allowed the unambiguous identification of tumor-bearing subjects.

The experiments conducted in humans indicate sufficiently sharp changes in fat metabolism of the cancer-bearing host (as compared with normal individuals and a small group of patients suffering from non-neoplastic diseases) as to have excellent diagnostic value. The changes observed in humans appear to be slightly different from those observed in mice bearing the Krebs-2 carcinoma. This is not surprising if one bears in mind a few fundamental considerations.

First, and most important, the human data pertain only to one point on the carbon-14 dioxide excretion curve, namely, sixteen hours after administration of the label. This point has been selected to produce maximum separation of the cancer data from the non-cancer data. Integration of the specific activity curves over 24-hours tends to show that, overall, cancer patients excrete less carbon-14 dioxide than controls, thus being consistent with the animal model. Since the data for *total* carbon dioxide excretion was not determined, cumulative 24-hour excretion values are not presented here. Furthermore, it should be considered that the label was introduced intraperitoneally in mice and orally in man which may account for some difference. A wider separation of the data relative to cancer patients and to patients without cancer may be obtained by intravenous administration of labelled fatty acids or labelled fatty acid precursors. With these considerations in mind, the difference between the data obtainable from human experimentation and those obtainable from experimentation with mice are not substantial.

The principles, preferred embodiments, and modes of operation of the present invention have been described in the foregoing specification. The invention which is intended to be protected herein, however, is not to be construed as limited to the particular forms disclosed since these are to be regarded as illustrative rather than restrictive. Variations and changes may be made by those skilled in the art without departing from the spirit or scope of the present invention.

What is claimed:

1. A diagnostic test method for detecting malignant neoplasms employing as a tracer a radioactively labelled lipid selected from the group consisting of fatty acids, fat precursors, simple fats, phospholipids, steroids and sterols, the label being a stable or unstable isotope selected from the group consisting of carbon, hydrogen, oxygen and phosphorus wherein the metabolism of said lipid by subjects having malignant neoplasms is different than in subjects not having such neoplasms comprising:
   a. administering to a subject under controlled conditions a predetermined amount of a radioactively labelled lipid tracer, capable of being metabolized by the subject;
   b. waiting a sufficient time to allow for the metabolism of the labelled lipid tracer; and
   c. determining by radioactive measurements the amount of radioactive catabolites in the excretion products.

2. The diagnostic test method of claim 1 wherein the excretion products are selected from the group consisting of urinary and respiratory excretion products.

3. The diagnostic test method of claim 2 wherein the excretion products are urinary excretion products.

4. A diagnostic test method for detecting malignant neoplasms comprising:
   a. administering to a subject, under controlled conditions, an analytically significant amount of a labelled lipid tracer selected from the group consisting of fatty acids, fat precursors, simple fats, phospholipids, steroids and sterols, wherein the labelled tracer atom is selected from the group consisting of phosphorous-32, carbon-13, carbon-14, oxygen-18, deuterium, tritium; and
   b. waiting a sufficient time after administration to allow for the metabolism of the labelled tracer; and
   c. analyzing the excretion products of the subject for labelled compounds.

5. The diagnostic test method of claim 4 wherein the lipid tracer is selected from the group consisting of fat precursors, fatty acids and simple fats.

6. The diagnostic test method of claim 5 wherein the simple fats are selected from the group of mono-, di- or triglycerides of naturally occurring fatty acids.

7. The diagnostic test method of claim 6 wherein the simple fat is selected from the group consisting of mono-, di-, and triglycerides of oleic, stearic and palmitic acids.

8. The diagnostic test method of claim 5 wherein the fat precursor is acetate.

9. The diagnostic test method of claim 5 wherein the fatty acid is selected from the group consisting of saturated and unsaturated acids having a carbon chain length of from two to about 22.

10. The diagnostic test method of claim 9 wherein the fatty acid is a naturally occurring fatty acid.

11. The diagnostic test method of claim 10 wherein the naturally occurring fatty acid is selected from the group consisting of oleic, stearic, palmitic, linoleic, linolenic and arachidonic acids.

12. The diagnostic test method of claim 5 wherein the waiting period after administration is at least $\frac{1}{2}$ hour.

13. A diagnostic test method of claim 5 wherein the labelled tracer atom is selected from the group consisting of carbon-13 and carbon-14.

14. The diagnostic test method of claim 4 wherein the administration of the labelled lipid tracer is intravenous or intramuscular.

15. A diagnostic test method for detecting malignant neoplasms comprising:
   a. orally administering to a fasting subject, under controlled conditions, from about 3 to about 80 microcuries per subject of a carbon-14 labelled tripalmitin tracer;
   b. continuing said fasting by the subject for from about two to about six hours;
   c. waiting for an additional period of time such that the total period from the time of administration is from about 14 to about 18 hours to allow for the metabolism of the tripalmitin tracer; and
   d. analyzing the respiratory excretion products of the subject by slowly bubbling a quantitative amount of exhaled breath through an ethanol/methylcellosolve solution of known concentration until fully saturated with carbon dioxide, adding an appropriate amount of a scintillation solution, and recording the amount of carbon-14 labelled product in a liquid scintillation counter.

16. The diagnostic test method of claim 15 wherein the scintillation solution comprises toluene/methylcellosolve/2,5-diphenyloxazole.

17. A diagnostic test method for detecting malignant neoplasms employing a radioactively labelled lipid wherein the metabolism of said lipid by subjects having malignant neoplasms is different than in subjects not having such neoplasms comprising:
   a. administering to a subject under controlled conditions, a predetermined amount of a radioactively labelled lipid tracer, capable of being metabolized by the subject;
   b. waiting a sufficient time to allow for the metabolism of the labelled lipid tracer; and
   c. determining by scintillation detection the amount of radioactive catabolites in the respiratory excretion products.

18. A diagnostic test method for detecting malignant neoplasms comprising:
   a. administering to a subject, under controlled conditions, an analytically significant amount of a labelled lipid tracer selected from the group consisting of fatty acids, fat precursors, simple fats, wherein the labelled tracer atom is selected from the group consisting of phosphorous-32, carbon-13, carbon-14, oxygen-18, deuterium, tritium; and
   b. waiting a sufficient time after administration to allow for the metabolism of the labelled tracer; and
   c. analyzing the respiratory excretion products of the subject for labelled compounds by scintillation detection.

* * * * *